United States Patent [19]

Shepherd

[11] Patent Number: 5,162,116
[45] Date of Patent: Nov. 10, 1992

[54] INTRA-RUMINAL DEVICE FOR DELIVERING DRUGS

[75] Inventor: Michael T. Shepherd, Berkhamsted, England

[73] Assignee: Coopers Animal Health Limited, Hertfordshire, United Kingdom

[21] Appl. No.: 794,647

[22] Filed: Nov. 18, 1991

Related U.S. Application Data

[63] Continuation of Ser. No. 448,097, Dec. 12, 1989, abandoned.

[30] Foreign Application Priority Data

Dec. 13, 1988 [GB] United Kingdom ............... 8829089

[51] Int. Cl.$^5$ .................. A61D 7/00; A61M 31/00; A61K 9/00
[52] U.S. Cl. .................. 424/438; 424/422; 604/135; 604/143; 604/150
[58] Field of Search ............... 424/438; 604/135, 143, 604/150

[56] References Cited

U.S. PATENT DOCUMENTS

| | | | |
|---|---|---|---|
| 4,675,174 | 6/1987 | Eckenhoff | 424/438 |
| 4,772,474 | 9/1988 | Eckenhoff | 424/438 |

FOREIGN PATENT DOCUMENTS

| | | |
|---|---|---|
| 149510 | 7/1985 | European Pat. Off. |
| 174865 | 3/1986 | European Pat. Off. |

*Primary Examiner*—Thurman K. Page
*Assistant Examiner*—E. J. Webman
*Attorney, Agent, or Firm*—Nixon & Vanderhye

[57] ABSTRACT

An intraruminal device for controlled release of a drug formulation in the rumen of an animal, comprises an open-ended tube for containing the drug formulation, a piston adapted to travel longitudinally within the tube and biased so as to deliver the drug formulation through the open end of the tube. Travelling with the piston is an associated weight adapted to retain the device within the rumen during delivery of the drug formulation.

10 Claims, 1 Drawing Sheet

INTRA-RUMINAL DEVICE FOR DELIVERING DRUGS

This is a continuation of application Ser. No. 07/448,097 filed Dec. 12, 1989, now abandoned.

This invention relates to an intra-ruminal device for delivering a formulation of a drug, growth promotant, vitamin or mineral (hereinafter referred to generically as "drugs") to a ruminant.

It is known that the rumen is a suitable site for the administration of drugs to a ruminant. The drug formulation can be injected directly into the rumen through the flank of the animal. Alternatively, a mechanical device or bolus can be introduced via the mouth of the animal, in which case it is desirable for the device or bolus to be retained within the reticulo-rumen ("rumen") for controlled release of the drug formulation thereafter. One method of retaining the device within the rumen is to arrange for its geometry to alter once it is in the rumen, for example for wings to extend laterally from the main body of the device to retard or prevent regurgitation thereof by the animal. Alternatively, the bolus or device may be made sufficiently dense for it to be retained in the rumen simply by the action of gravity. One such device of the latter type is disclosed in EP-A-149 510 (Eli Lilly & Company) where a substantially solid drug formulation is contained within a generally tubular body having an open end and a closed end. A spring-biassed piston urges the formulation towards the open end whereupon it is gradually eroded by the rumen fluids. The spring for the piston is wrapped around a heavy cylindrical weight which is fixed to the main tubular body of the device.

It has now been found that distinct advantages may accrue from associating the weight, which is used to impart the desirable density to the overall device, with the piston rather than with the main body of the device.

According, one aspect of the present invention provides an intra-ruminal delivery device comprising: a tube having a substantially closed end and a substantially open end and adapted to contain a drug formulation for controlled release thereof through the open end of the tube; a piston adapted to travel longitudinally within the tube; and biassing means to bias the piston towards the open end of the tube, the piston being associated with a weight for movement therewith, the weight being adapted to retain the device within the rumen of a ruminant during delivery of the drug formulation.

In one particular embodiment, the weight is a separate element located adjacent the piston, preferably on the surface thereof remote from the biassing means.

Alternatively, the weight may be constituted by the piston itself. For example, the piston may be die-cast of zinc or of a zinc-containing alloy such as to have the desired mass. Alternatively, the piston may comprise a chamber containing metal shot, in which case the piston itself may be lighter and may be made of a plastics material. This chamber may be sealed or it may open towards the drug formulation on the side of the piston remote from the biassing means.

The biassing means may comprise a compression spring, a gas-filled chamber having a higher than atmospheric pressure within, a polymer which swells on contact with rumen fluids, or a means for pressure to build up by osmosis of gas or liquid from the rumen into a chamber behind the piston.

A further aspect of the invention provides a device as above additionally comprising a drug formulation. A still further aspect provides a method of administering a drug to a ruminant by causing a device as above, loaded with the drug formulation, to be located within the ruminant's rumen.

It has been found that advantages related to ease of manufacture may be derived from devices in accordance with the invention. It has also been found that it is possible to arrange for the weight which is associated with the piston to be separated from the tubular body of the device once the drug formulation has been exhausted. For example, a separate heavy element between the piston and the drug formulation may simply be expelled from the device. Alternatively, in the embodiment where an open shot-filled chamber is provided, the shot will be dispersed. Yet again, where the piston itself embodies the weight, then the piston may be forced out of the tubular body by the biassing means. In any event, the weight which is causing the device to be retained within the rumen may be separated from the remainder of the device, with the latter thereupon being regurigitated by the animal. Thus, a reduced amount of debris is left within the rumen, thereby reducing the likelihood of interference with the further processing of the animal when it comes to the end of its days in an abattoir.

So that the invention may be more readily understood and so that certain features thereof may become more readily apparent, preferred embodiments of the invention will now be described by way of example and by reference to the accompanying drawings, in which.

Figure 1:
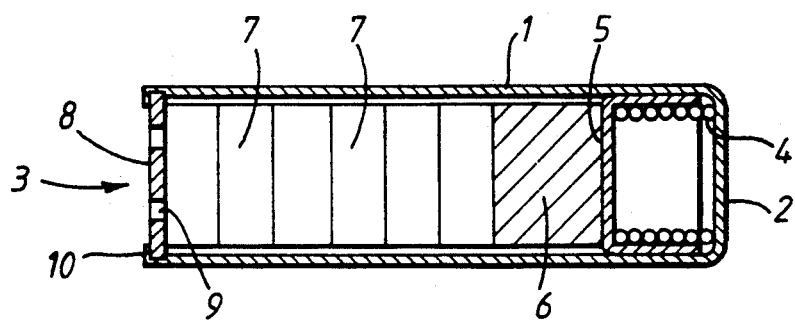
FIG. 1 is a diagrammatic longitudinal cross-section of a device in accordance with the invention.

The device illustrated in FIG. 1 comprises a tubular body 1 having a closed end 2 and a substantially open end 3. Inside and adjacent the closed end 2, there is a compression spring 4 which acts to force apart the closed end 2 of the body 1 and a piston 5 which is arranged for longitudinal sliding motion within the body 1. On the side of the piston 5 remote from the spring 4 there is a generally cylindrical element 6 having a diameter slightly smaller than the internal diameter of the body 1 and being arranged coaxially therewith. The element 6 is formed of a dense metallic material such as mild steel. Between the dense element 6 and the open end 3 of the body 1, there is a plurality of discs 7, at least one of which is formed of a drug formulation. Advantageously, the drug formulation comprises glucose monostearate. The disc 7 adjacent the open end 3 of the body 1 is held within the body by means of a retaining plate 8, perforated by a plurality of holes 9, which is in turn held in the open end 3 of the body 1 by virtue of an inwardly crimped annular flange 10.

The device is delivered down the oesophagus of a ruminant, for example by using a suitable balling gun, and lodges in the rumen by virtue of the overall density of the device. By means of a process well known in this art, the ruminal fluids enter the device through the holes 9 in the end plate 8 and cause the glucose monostearate to swell and soften thus enabling the formulation to be extruded through the holes 9 under the action of the compression spring 4. Successive discs 7 are continuously brought towards the open end 3 of the body 1 of the device and thereby into contact with the ruminal fluids. Respective discs 7 may contain differing drugs or differing levels of drugs, and indeed some discs may contain no drug at all, so that a pulsed delivery of one or more drugs may be achieved. Alternatively, the discs 7 may be replaced by a single cylindrical block of the drug formulation. The end plate 8 may be made of a suitable alloy, for example magnesium-containing alloy, which will itself be eroded gradually by the action of the rumen fluids, but at a rate considerably slower than the erosion or dissolution of the drug formulation. Thereby, once all of the drug formulation and the end plate 8 have gone, the dense element 6 may be expelled from the end of the device, optionally followed also by the piston 5 and indeed the compression spring 4, if desired, although there is a danger of puncturing the rumen if the spring is lost from the cylinder. Alternatively, the end-plate 8 is made of plastics or aluminium and is not eroded.

It may be desirable to prevent low pressure forming behind the piston, which might otherwise oppose the action of the spring, by having a small hole in the closed end 2 of the body. Clearly, in such an embodiment, the piston should not be made of a biodegradable material and should have a sufficiently tight seal with the body to prevent rumen fluids oozing past the piston and into contact with the drug formulation.

In a variation of this embodiment the end plate 8 is dispensed with and, instead, the drug formulation discs 7 are retained in the device simply by the flange 10. Clearly, if it is desired for the dense element 6 to be ejected from the device after all the formulation has gone, then the length of the flange 10 and the diameter of the element 6 must be chosen appropriately. It is to be remembered that expulsion of the dense element 6 is not an essential feature of the invention; manufacturing advantages may accrue simply from having the weight associated with the piston.

Figure 2:
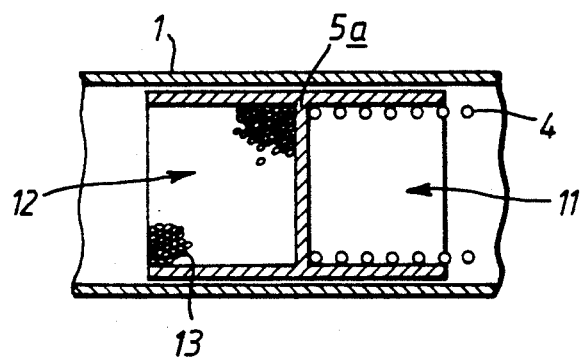
FIG. 2 is a diagrammatic longitudinal cross-section of part of a second device in accordance with the invention.
Figure 3:
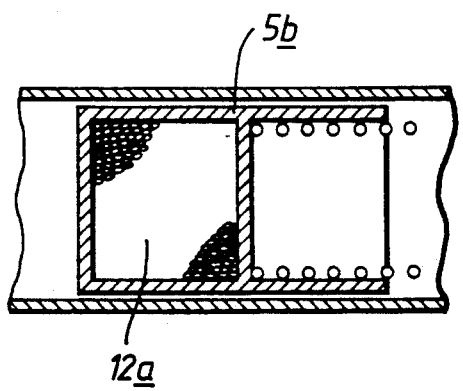
FIG. 3 is a diagrammatic longitudinal cross-section of part of a third device in accordance with the invention, being a variation of the second device shown in FIG. 2.

FIG. 2 illustrates part of a second embodiment of the invention where, for simplicity, only the piston 5a, the spring 4 and the body 1 of the device are shown. The piston 5a has a generally "H" cross-section, such as to define respective cup-shaped cavities 11, 12 to accommodate the compression spring 4 and a plurality of shot particles 13. The shot particles 13 are formed of a suitably dense material, for example iron. The operation of the device is essentially the same as with the device of FIG. 1, except that it can be seen that, once all of the drug formulation discs 7 have been dissolved away, the shot 13 will be free to fall out of the body 1 of the device. The overall density of the device will thereby be lessened, preferably to a sufficient extent to allow the device to be regurgitated from the rumen, leaving simply the shot 13 in the rumen. In the embodiment shown in FIG. 3, the arrangement is substantially the same as in FIG. 2 except that the cup-shaped chamber 12a in the piston 5b containing the shot 13 is sealed. The sealing (or the whole piston) is advantageously made of a biodegradable material such as ICI's "Polyox".

Figure 4:
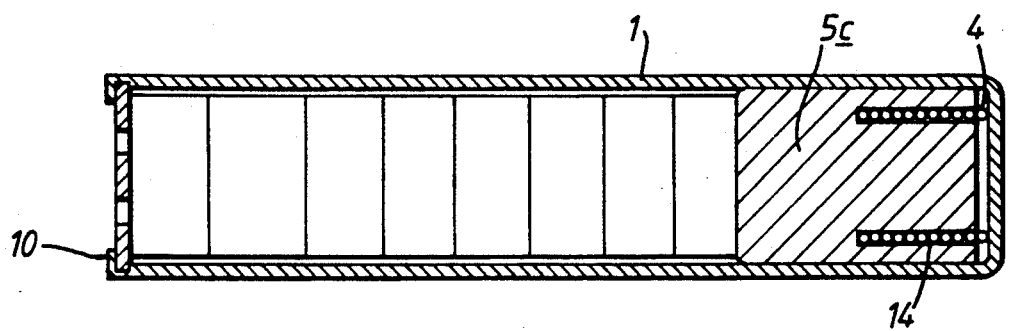
FIG. 4 is a diagrammatic longitudinal cross-section of a fourth device in accordance with the invention.

Finally, in the embodiment illustrated in FIG. 4, the piston 5c is sufficiently massive to provide the desired weight itself and is die-cast from zinc or a zinc-containing alloy. In the preferred arrangement shown in FIG. 4, the piston 5c is provided with an annular channel 14 to accommodate and assist the action of the compression spring 4. As described above, by suitably choosing the diameter of the piston 5c and the extent of the flange 10, the piston (and, optionally, the compression spring 4) may be ejected, or not, once all of the drug formulation has been dispensed.

The various features of the embodiments described by reference to FIGS. 1 to 4 may be combined with one another in suitable ways. For example, the shot-filled chamber arrangement of FIG. 2 may be supplemented by a separate dense element 6, if desired.

Devices in accordance with the invention may be used to dispense, optionally in a pulsed fashion, drugs such as anthelmintics (particularly oxfendazole), growth promotants such as tetronasin, vitamins and trace minerals, such as magnesium, cobalt, copper and selenium.

I claim:

1. An intra-ruminal delivery device comprising:
   a tube having a partly or completely closed end and a partly or completely open end and a drug formulation for controlled release thereof through the open end of the tube;
   a piston adapted to travel longitudinally within the tube, the drug formulation located between the open end of the tube and the piston;
   a means for biasing the piston towards the open end of the tube; and
   a weight retaining the device within the rumen of a ruminant during delivery of the drug formulation and located on the surface of the piston remote from the biasing means, the weight being separable from the piston whereby the weight is expelled from the device from the open end following release of the drug formulation.

2. A device according to claim 1, wherein the weight comprises shot contained in a chamber located in the surface of the piston remote from the spring, said chamber opening into the interior of the tube.

3. A device according to claim 1, additionally including a drug formulation.

4. A method of administering a drug to a ruminant by causing a device according to claim 1 to be located within the ruminant's rumen.

5. An intra-ruminal delivery device comprising:
   a tube having a partially or completely closed end and a partially or completely open end and a drug formulation for controlled release thereof through the open end of the tube;
   a piston of sufficient weight to retain the device within the rumen of a ruminant during delivery of the drug formulation and adapted to travel longitudinally within the tube and be expelled from the open end of the tube following release of the drug formulation, the drug formulation located between the open end of the tube and the piston; and
   a means for biasing the piston towards the open end of the tube.

6. A device according to claim 5, wherein the piston is die-cast of zinc or of a zinc-containing alloy.

7. A device according to claim 5, wherein the piston comprises a chamber containing shot.

8. A device according to claim 7, wherein the chamber is sealed.

9. A device according to claim 5, additionally including a drug formulation.

10. A method of administering a drug to a ruminant by causing a device according to claim 5 to be located within the ruminant's rumen.

* * * * *